US009927060B2

United States Patent
Moses et al.

(10) Patent No.: US 9,927,060 B2
(45) Date of Patent: Mar. 27, 2018

(54) VEHICLE FOR NAVIGATING WITHIN AN ENCLOSED SPACE

(71) Applicant: The Johns Hopkins University, Baltimore, MD (US)

(72) Inventors: Matthew S. Moses, Lafayette, CO (US); Christopher Y. Brown, Olney, MD (US); Charbel G. Rizk, Sykesville, MD (US); Jason E. Tiffany, Columbia, MD (US); Michael D. Kutzer, Baltimore, MD (US); David H. Scheidt, Edgewater, MD (US)

(73) Assignee: The Johns Hopkins University, Baltimore, MD (US)

( * ) Notice: Subject to any disclaimer, the term of this patent is extended or adjusted under 35 U.S.C. 154(b) by 20 days.

(21) Appl. No.: 15/133,251

(22) Filed: Apr. 20, 2016

(65) Prior Publication Data

US 2016/0310223 A1 Oct. 27, 2016

Related U.S. Application Data

(60) Provisional application No. 62/150,922, filed on Apr. 22, 2015.

(51) Int. Cl.
| | | |
|---|---|---|
| *F16L 55/34* | (2006.01) | |
| *A61B 34/30* | (2016.01) | |
| *A61B 1/00* | (2006.01) | |
| *A61B 1/04* | (2006.01) | |

(52) U.S. Cl.
CPC ........... *F16L 55/34* (2013.01); *A61B 1/00108* (2013.01); *A61B 1/00156* (2013.01); *A61B 1/041* (2013.01); *A61B 2034/302* (2016.02)

(58) Field of Classification Search
CPC .............. F16L 55/34; A61B 2034/302; A61B 1/00108; A61B 1/00156; A61B 1/041
See application file for complete search history.

(56) References Cited

U.S. PATENT DOCUMENTS

| | | | | |
|---|---|---|---|---|
| 4,006,359 A | * | 2/1977 | Sullins .................. | G01M 3/005 104/138.2 |
| 4,919,223 A | * | 4/1990 | Egger ................... | G01M 3/005 104/138.2 |
| 5,375,530 A | * | 12/1994 | Zollinger ............... | F16L 55/26 104/138.1 |
| 5,791,255 A | * | 8/1998 | Box ........................ | F16L 55/34 104/138.2 |
| 5,899,795 A | * | 5/1999 | Penza .................. | B23D 79/023 15/104.09 |

(Continued)

*Primary Examiner* — Joseph M Rocca
*Assistant Examiner* — Michael R Stabley
(74) *Attorney, Agent, or Firm* — Noah J. Hayward

(57) ABSTRACT

A vehicle includes a head section having a selectively actuated first plurality of claws, a tail section having a selectively actuated second plurality of claws, and a linear actuator operably coupling the head section to the tail section. The linear actuator is configured to be selectively extended and retracted. The vehicle is configured to move forward within an enclosed space by extending the linear actuator, while the first plurality of claws is not actuated and the second plurality of claws is actuated, then retracting the linear actuator, while the first plurality of claws is actuated and the second plurality of claws is not actuated.

19 Claims, 6 Drawing Sheets

(56) References Cited

U.S. PATENT DOCUMENTS

| | | | |
|---|---|---|---|
| 5,947,213 A * | 9/1999 | Angle | E21B 4/18 |
| | | | 166/250.01 |
| 6,098,231 A | 8/2000 | Smith et al. | |
| 6,162,171 A * | 12/2000 | Ng | A61B 1/00156 |
| | | | 600/101 |
| 6,415,722 B1 * | 7/2002 | Reis | B08B 9/049 |
| | | | 104/138.2 |
| 6,427,602 B1 * | 8/2002 | Hovis | F16L 55/34 |
| | | | 104/138.1 |
| 6,450,104 B1 | 9/2002 | Grant et al. | |
| 6,870,343 B2 * | 3/2005 | Borenstein | B08B 9/045 |
| | | | 180/9.21 |
| 6,917,176 B2 | 7/2005 | Schempf et al. | |
| 6,944,902 B1 * | 9/2005 | Richter | B08B 9/0551 |
| | | | 15/104.061 |
| 7,143,659 B2 | 12/2006 | Stout et al. | |
| 7,182,025 B2 | 2/2007 | Ghorbel et al. | |
| 7,210,364 B2 | 5/2007 | Ghorbel et al. | |
| 7,594,448 B2 | 9/2009 | Jacobson et al. | |
| 7,597,048 B2 * | 10/2009 | Nicholson | B08B 9/035 |
| | | | 104/138.2 |
| 7,617,558 B2 * | 11/2009 | Boe | B08B 9/049 |
| | | | 15/104.061 |
| 7,798,023 B1 * | 9/2010 | Hoyt | F16L 55/28 |
| | | | 73/865.8 |
| 8,042,630 B2 | 10/2011 | Jacobsen | |
| 8,402,911 B1 * | 3/2013 | Weisenberg | F16L 55/265 |
| | | | 104/138.2 |
| 8,571,711 B2 | 10/2013 | Jacobsen et al. | |
| 8,950,338 B2 * | 2/2015 | Early | F16L 55/32 |
| | | | 104/138.1 |
| 9,353,902 B2 * | 5/2016 | Early | F16L 55/265 |
| 9,409,292 B2 * | 8/2016 | Smith | B25J 9/065 |
| 2006/0064829 A1 | 3/2006 | Houldey et al. | |
| 2014/0020594 A1 * | 1/2014 | Early | F16L 55/265 |
| | | | 105/26.05 |
| 2014/0121835 A1 | 5/2014 | Smith | |
| 2015/0375276 A1 | 12/2015 | Sivacoe | |

* cited by examiner

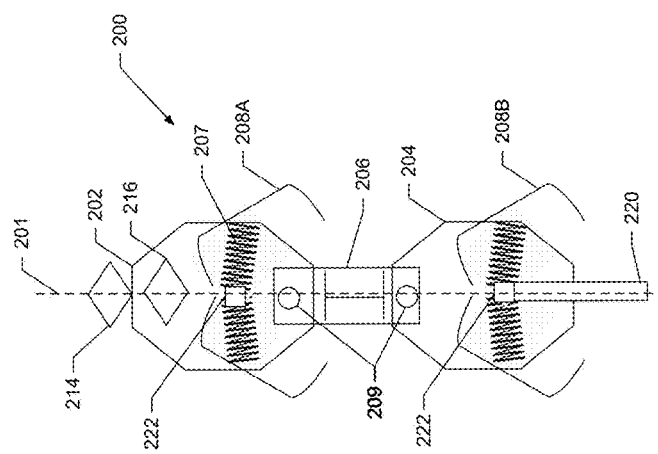
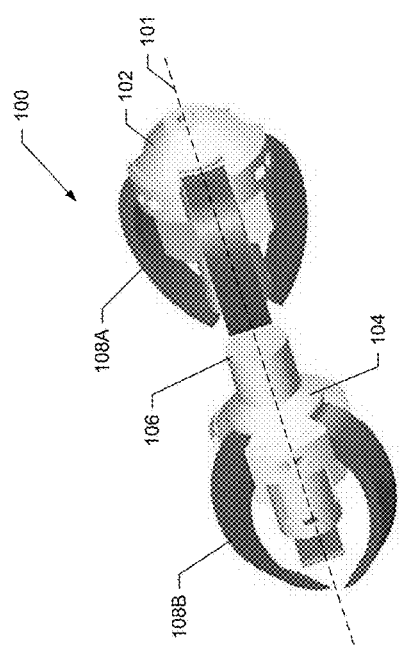

VEHICLE FOR NAVIGATING WITHIN AN ENCLOSED SPACE

CROSS REFERENCE TO RELATED APPLICATIONS

This application claims the benefit of U.S. Provisional Application No. 62/150,922 filed on Apr. 22, 2015, the entire contents of which are hereby incorporated herein by reference.

STATEMENT OF GOVERNMENTAL INTEREST

This invention was made with Government support under contract number FA8620-08-G-4030 awarded by the U.S. Air Force. The Government has certain rights in the invention.

TECHNICAL FIELD

Example embodiments generally relate to vehicles and, in particular, relate to a vehicle for navigating within an enclosed space.

BACKGROUND

Unmanned vehicles configured to navigate enclosed spaces, such as pipes, e.g. fluid or gas pipes, may be small. Thus the types of locomotion which may be effectively employed on such vehicles may be limited by size constraints. In some examples, a plurality of wheels positioned around a perimeter of a vehicle may be used to move the vehicle through an enclosed space. However, wheeled vehicles may be limited in use to a specific diameter pipe.

In another example, a complicated crawler system may be used. In one crawler system, a series of bumpers maintain the vehicle centrally located in a pipe. Separately, pressure pads may be used to hold one of two gripping modules stationary while a locomotion module expands or contracts to move the vehicle. However, the stroke length of the pressure pad actuators and/or the bumper length may limit the minimum or maximum diameter pipe in which the vehicle may be effectively deployed. Further, the vehicle requires separate holding mechanisms and centering devices.

BRIEF SUMMARY OF SOME EXAMPLES

Accordingly, in some example embodiments, a vehicle is provided including a head section including a selectively actuated first plurality of claws; a tail section including a selectively actuated second plurality of claws; and a linear actuator operably coupling the head section to the tail section. The linear actuator is configured to be selectively extended and retracted. The vehicle is configured to move forward within an enclosed space by extending the linear actuator, while the first plurality of claws is not actuated, and the second plurality of claws is actuated, then retracting the linear actuator, while the first plurality of claws is actuated and the second plurality of claws is not actuated.

BRIEF DESCRIPTION OF THE SEVERAL VIEWS OF THE DRAWING(S)

Having thus described the vehicle in general terms, reference will now be made to the accompanying drawings, which are not necessarily drawn to scale, and wherein:

FIG. 1A illustrates a vehicle configured to navigate in an enclosed space according to an example embodiment.

FIG. 1B illustrates cross-sectional diagram of a vehicle configured to navigate an enclosed space.

DETAILED DESCRIPTION

Figure 1C:
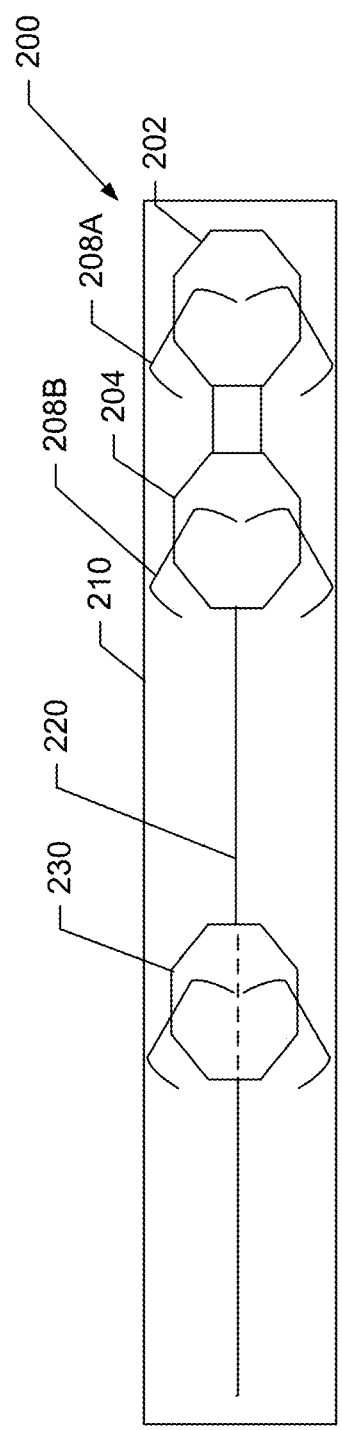
FIG. 1C illustrates an example vehicle with detachable sections according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

As used in herein, the terms "component," "module," and the like are intended to include a computer-related entity, such as but not limited to hardware, firmware, or a combination of hardware and software. For example, a component or module may be, but is not limited to being, a process running on a processor, a processor, an object, an executable, a thread of execution, and/or a computer. By way of example, both an application running on a computing device and/or the computing device may be a component or module. One or more components or modules may reside within a process and/or thread of execution and a component/module may be localized on one computer and/or distributed between two or more computers. In addition, these components may execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or may be operably coupled to, the processing circuitry to modify the behavior and/or capability of the processing circuitry based on the hardware and/or software that is added to or otherwise operably coupled to the processing circuitry to configure the processing circuitry accordingly.

In an example embodiment, a vehicle is provided for navigating an enclosed space, such as a pipe. In some instances the pipe may be a water or gas pipe. However the vehicle may be scaled to allow for navigation of any size pipe, or other similar enclosed space. In some instances, the vehicle may be deployed in biological environments, such as a colon, small intestine, large intestine, circulatory system, or the like. The vehicle may include a head section and a tail section operably coupled by a linear actuator. The head section and tail section each include a plurality of claws. The claws may hold the head section or tail section in position when actuated and allow movement when not actuated. The linear actuator may be configured to repeatedly extend and retract causing the vehicle to move forward in an inchworm like manner.

The claws may be capable of extending to various distances, allowing for the vehicle to navigate different size pipes and/or navigate around obstacles. Additionally, the ability to extend the claws to different distances may allow the vehicle to maneuver around debris, instead of pushing the debris further in the pipe, or becoming stuck in the pipe due to the debris.

In one example embodiment, the claws may be biased outward from the head section or tail section, such as by a spring. The spring may allow for the claws to move toward the head section or tail section during forward movement, and engage the side wall of the pipe, e.g. actuate, when a force is applied in the backward direction. In some embodiments, the claws may also include a switchable lock configured to cause the claws to allow movement in the backward direction and actuate inhibiting movement in the forward direction.

In some example embodiments, one or more actuators may be provided to actuate the claws and/or assist the spring in actuation of the claws. For example, a linear actuator may be used to increase the force applied to the side wall of the pipe to maintain a position of the head section or tail section during movement and/or work.

In an example embodiment, the vehicle may include one or more working elements and/or sensors. The working elements may include cutting tools which may be employed to remove a blockage perform, cutting operations, or the like or grabbers, which may grab an object in the pipe, hold an object, such as a wire, while navigating the pipe, or the like. Sensors may include a camera to capture images within the pipe, measuring devices, proximity detectors and/or range detectors, which may be employed to measure distance to objects from known points, wall thickness, or the like Example Vehicle An example embodiment of the vehicle will now be described in reference to FIG. 1A, which illustrates an example vehicle 100 configured to navigate an enclosed space. The vehicle 100 may include a head section 102 and a tail section 104. The head section 102 may be operably coupled to the tail section 104 by a linear actuator 106. The head section 102 may include a first plurality of claws 108A and the tail section 104 may include a second plurality of claws 108B.

The vehicle 100 may be configured to navigate an enclosed space, such as a pipe. In an instance in which the vehicle 100 is configured to move forward, the linear actuator 106 may be extended while, the first plurality of claws 108A is not actuated and the second plurality of claws 108B is actuated. The second plurality of claws 108B may inhibit motion of the tail section 104 during the extension of the linear actuator 106, while the first plurality of claws 108A may allow forward movement of the head section 102. Next, the linear actuator 106 may retract while the first plurality of claws 108A is actuated and the second plurality of claws 108B is not actuated. The first plurality of claws 108A may inhibit motion of the head section 102 during the retraction of the linear actuator 106, while the second plurality of claws 108B may allow forward movement of the tail section 104. The extension and retraction of the linear actuator may include an expansion and contraction of the linear actuator 106 in a longitudinal axis 101 of the vehicle 100. The vehicle 100 may repeat the process, as necessary, to move to a desired position or a desired distance, in an inchworm like manner.

In an example embodiment, the vehicle 100 may be configured to move backward in the enclosed space. The vehicle 100 may move backward by extending the linear actuator 106 while, the second plurality of claws 108B is not actuated and the first plurality of claws 108A is actuated. The first plurality of claws 108A may inhibit motion of the head section 102 during the extension of the linear actuator 106, while the second plurality of claws 108B may allow rearward movement of the tail section 104. Next, the linear actuator 106 may be retracted, while, the first plurality of claws 108A is not actuated and the second plurality of claws 108B is actuated. The second plurality of claws 108B may inhibit motion of the tail section 104 during the retraction of the linear actuator 106, while the first plurality of claws 108A may allow rearward movement of the head section 102.

In an example embodiment, the first plurality of claws 108A may be configured to extend approximately the same distance away from the head section 102 when extended. In some example embodiments, the first plurality of claws 108A may be operably coupled, or otherwise configured for approximately identical or symmetrical movement or extension about a longitudinal axis 101. The second plurality of claws 108B may be configured similar to the first plurality of claws 108A relative to the tail section 104. The extension of the plurality of claws 108A, 108B approximately the same distance may cause the head section 102 and/or tail section 104 to be substantially centered in the enclosed space. Thus, the longitudinal axis 101 of the vehicle 100 aligns with a longitudinal extension of the pipe or enclosed space.

In an example embodiment, the first plurality of claws 108A and second plurality of claws 108B may be configured to extend radially outward to a plurality of distances from the longitudinal axis 101 of the head section 102 or tail section 104, respectively. The range of extension of the first plurality of claws 108A and the second plurality of claws 108B may enable the vehicle to be deployed in enclosed spaces of various sizes, such as pipes with diameters of 1 inch, 1.5 inches, 2 inches, 3 inches, or the like. Additionally, the vehicle 100 may be capable of navigating a pipe with multiple diameters. Although, the vehicle 100 is described herein for navigation of water pipes or gas pipes, one of ordinary skill in the art would immediately appreciate that the vehicle is scalable for application in larger applications and smaller applications. The first plurality of claws 108A or second plurality of claws 108B may include three claws, four claws, five claws, or the like.

In an example embodiment, each of the claws 108A, 108B may be defined by a complex curve. The complex curve may allow for each of the claws 108A, 108B to have sufficient gripping surface with a sidewall of the pipe over a full range of extension of each claw 108A, 108B from the head section 102 or tail section 104, while accounting for load induced deflection of the material.

The example vehicle 100, as discussed herein, including the head section 102 and a tail section 104 is merely for illustrative purposes, one of ordinary skill in the art would immediately appreciate that a vehicle 100 may include any number of sections, such as three sections, four sections, or the like. In some example embodiments, one or more sections may not include claws 108A, 108B.

FIG. 1B illustrates a cross-sectional view of a vehicle 200 configured for navigation of an enclosed space. The vehicle 200 may include a head section 202 and a tail section 204 operably coupled to each other by a linear actuator 206. The head section 202 may include a first plurality of claws 208A and the tail section 204 may include a second plurality of claws 208B.

The linear actuator 206 may be an electromagnetic actuator, a hydraulic actuator, pneumatic actuator, mechanical actuator, or the like. In some instances the linear actuator 206 may be enclosed within a housing to prevent damage from the environment, such as water and/or debris. The linear actuator 206 may extend and retract along a longitudinal axis 201.

The head section 202 and/or tail section 204 may be operably coupled to the linear actuator 206 by a joint 209. The joint 209 may include a stiff joint, which may not allow movement between the linear actuator 206 and the head section 202 or tail section 204. In some example embodiments, the joint 209 may be an articulated joint or ball joint, which may allow for the head section 202 or/or the tail section 204 to move or pivot relative to the linear actuator 206. In an instance in which the joint 209 is an articulated joint, the vehicle 200 may be enabled to navigate turns or bends in the enclosed space.

In an example embodiment, the vehicle 200 may include a claw actuator operably coupled between the head section 202 or tail section 204 and each claw 208A, 208B. In some example embodiments, the claw actuator may include a spring 207 configured to bias the claws 208A, 208B away, e.g. radially outward, from the longitudinal axis 201 of the head section 202 or tail section 204, respectively. The spring 207 may be a compression spring, a leaf spring, spiral spring, torsion spring, or the like. The spring 207 may cause the claws 208A, 208B to actuate in an instance in which a force is applied in a first direction, such as backward (e.g. away from the head section 202 and toward the tail section 204), causing the claws 208A, 208B to actuate, e.g. engage the side walls of the pipe. In an example embodiment, the engagement of the claws 208A, 208B with the sidewall of the pipe increased with an increase of force applied in the first direction. In an example embodiment in which the claws 208A, 208B are constructed of a semi rigid material, the claws 208A, 208B may partially deform, which may increase the contact surface area of the claws 208A, 208B, with the sidewall of the pipe. The increase in contact surface area with the sidewall of the pipe may increase the friction between the sidewall of the pipe and the claws 208A, 208B, which increases the resistance to the force applied in the first direction.

In an instance in which force is applied to the claws in a second direction, such as forward (e.g. toward the head section 202 and away from the tail section 204), the claws 208A, 208B may compress the springs enabling the head section 202 or the tail section 204 to move in the second direction. In an example embodiment, the claws 208A, 208B may be operated or assisted in operation by claw linear actuators, which may extend or retract the claws 208A, 208B, as discussed below in reference to FIGS. 3-6. In an instance in which the claws 208A, 208B are retracted, the claws 208A, 208B may be near flush, flush or recessed in the head section 202 or tail section 204, respectively. Having the claws 208A, 208B about flush with the head section 202 or tail section 204, may enable the moving section (e.g. the head section 202 or tail section 204 which does not have actuated claws 208A, 208B) to have less friction with the side wall of the pipe.

In some example embodiments, a support for the spring 207 may shift when the spring 207 is not actuated to loosen the tension of the spring 207. Similarly, the support may shift when the spring 207 is actuated to tighten the tension of the spring 207. The change in the tension of the spring 207 may allow for force to be applied to the claws 208A, 208B by the spring 207, when actuated and little or no force to be applied to the claws 208A, 208B by the spring 207 when not actuated.

In an example embodiment, the claws 208A, 208B may be operable coupled to a selectable or switchable lock 222, such as a ratchet or a rocker lock. The lock 222 may allow for the claws 208A, 208B to be actuated in the second direction, e.g. forward, and not actuate in the first direction, e.g. backward.

Additionally or alternatively, the claw actuators may include one or more claw linear actuators, similar to linear actuator 206. In some embodiments, the claw linear actuators may assist the spring 207 by extending, thus increasing the force applied to the sidewall of the pipe in an instance in which the claws 208A, 208B are actuated; and/or reduce the force needed to compress the spring 207 by retracting. In an example embodiment which does not include the spring 207, the claw linear actuators may extend and retract to actuate the claws 208A, 208B.

In some example embodiments, the vehicle 200 may include a sensor 216. The sensor 216 may include a camera, a distance measurement device, a proximity detector, a range detector, or the like. The sensor 216 may be operably coupled to the head section 202 and/or the tail section 204. In some embodiments, the sensor 216 may be disposed within the head section 202. In an example embodiment, the sensor 216 may be mounted to a distal end of the head section 202 or the tail section 204.

Additionally or alternatively, the vehicle 200 may include a working element 214. The working element 214 may include a cutting tool, such as a drill, grinder, blade, or the like; or a grabber, such as a pincher, or the like. In some embodiments, the working element 214 may be operably coupled to a distal end of the head section 202 or the tail section 204.

In some example embodiments, the vehicle 200 may include a tether 220. The tether 220 may be operably coupled to the tail section 204 and/or the head section 202, such that when a force applied to the tether 220 pulling against the vehicle 200, the claws 208A, 208B retract. The retraction of the claws 208A, 208B, when the tether 220 is pulled, allows for extraction of the vehicle 200 from an enclosed space without the vehicle 200 navigating the enclosed space in the second direction. Additionally, the tether 220 and retraction of the claws 208A, 208B may allow for the vehicle 200 to be removed in an emergency or in an instance in which the vehicle 200 is stuck. In an example embodiment in which multiple sections are employed, one or more rear sections 230 may be detachable and utilized as a guide for tether 220 to reduce friction in both the first and second directions within an enclosed space 210, as depicted in FIG. 1C.

In an example embodiment, the vehicle 200 may be controlled autonomously without user input. In some embodiments, the vehicle 200 may be controlled or driven based on user input. In yet a further embodiment, the vehicle 200 may include both autonomous and user control. An example control circuitry diagram is provided below in reference to FIG. 2.

Example Control Diagram

Figure 2:
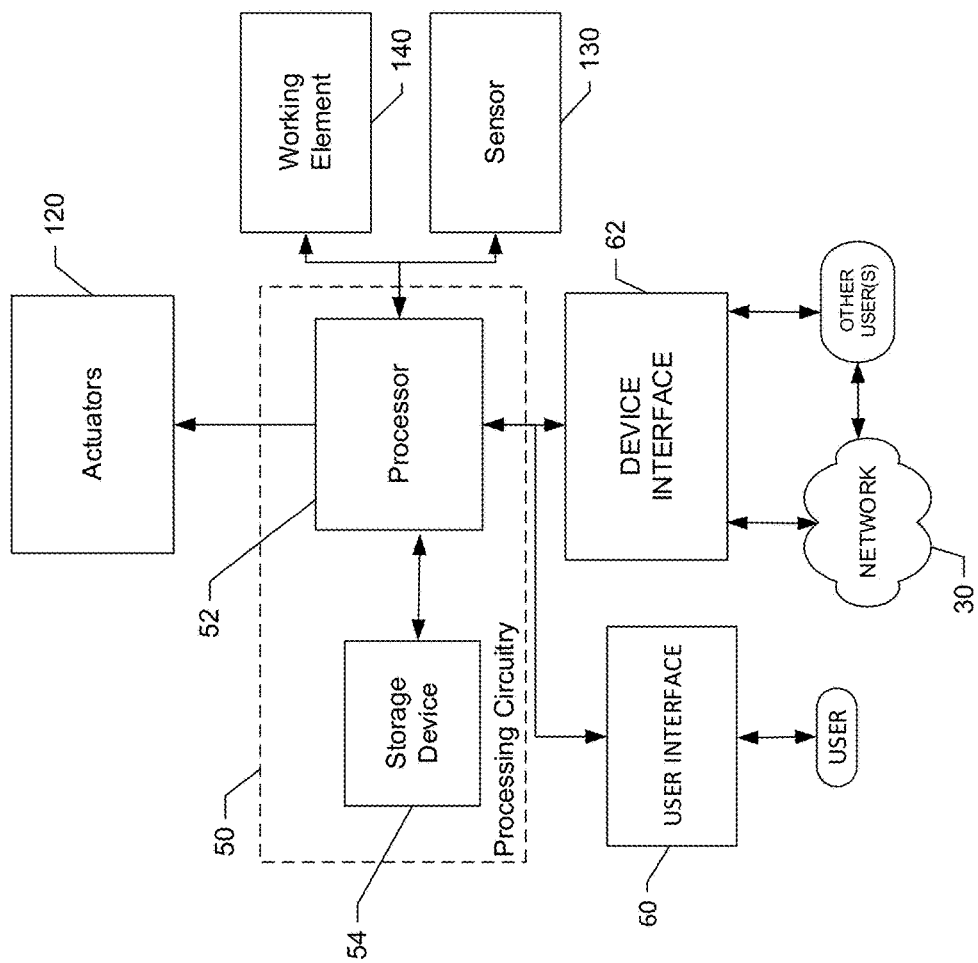
FIG. 2 illustrates an example control circuitry diagram for a vehicle according to an example embodiment.

FIG. 2 illustrates a control circuitry diagram for a vehicle, such as vehicle 200, configured to navigate an enclosed space according to an example embodiment. The control circuitry of FIG. 2 may be employed, for example, in on onboard circuitry, a variety of other devices (such as, for example, a network device, remote controller, or the like), or may be distributed among the onboard circuitry and the other devices. Furthermore, it should be noted that the devices or elements described below may not be mandatory and thus some may be omitted in certain embodiments.

In an example embodiment, the control circuitry may include or otherwise be in communication with processing circuitry 50 that is configured to perform data processing, application execution and other processing and management services according to an example embodiment. In one embodiment, the processing circuitry 50 may include a storage device 54 and a processor 52 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation, or even one of various mobile computing devices. In situations where the processing circuitry 50 is embodied as a server or at a remotely located computing device, the user interface 60 may be disposed at another device (e.g., at a computer terminal or client device such as one of the clients 20) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms. In embodiments where the apparatus is embodied at a server or other network entity, the user interface 60 may be limited or even eliminated in some cases. Alternatively, as indicated above, the user interface 60 may be remotely located.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network 30 and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with the network 30, the network 30 may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with example embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases that may store a variety of files, contents or data sets. Among the contents of the storage device 54, applications may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processing circuitry 50 may be in communication with one or more actuators 120. The actuators 120 may include a linear actuator, such as linear actuator 206 and one or more claw linear actuators. Additionally or alternatively, the actuators 120 may include one or more selectable or switchable locks configured to control the direction in which the claws, such as claws 208A, 208B, actuate to engage a side wall of the pipe. The processing circuitry 50 may be configured to control the actuation of each of the actuators 120 individually or in actuation groups, such as the first plurality of claws 208A and the second plurality of claws 208B. In an example embodiment, the claw linear actuators may provide a force feedback to the processing circuitry 50. The force feedback may be a function of current applied to the linear actuator or a pressure sensor, such as sensor 130 discussed below. In some instances the processing circuitry 50 may monitor and/or limit the pressure applied to the walls of the enclosed space. For example, the processing circuitry 50 may limit the pressure applied by the claw linear actuators when the vehicle 200 is deployed in a biological environment to prevent ripping or tearing of tissue, or when the vehicle 200 is deployed in a pipe with weak side walls, such as due to corrosion, to prevent rupturing the pipe.

Additionally or alternatively, the actuators 120 may include a steering device, such as one or more servo motor, as discussed below in reference to FIG. 8. The steering device may steer a head section, such as head section 202 toward an opening in a junction of a pipe or position sensors 130 or working elements 140.

In some example embodiments, the processing circuitry 50 may be in communication with one or more working elements 140. In some example embodiments, the working elements 140 may include a cutting tool. The cutting tool may include a drill, a grinder, a blade, or the like. The cutting tool may be utilized to clear obstructions on a pipe, cut a hole in the pipe, or other cutting operations. In an example embodiment, the working element 140 includes a grabber. The grabber may be a pincher, grasping claw, or the like. The grabber may be configured to grab or retain an object. In one example, the grabber may be configured to retain a wire, cable or the like, as the vehicle 200 navigates the pipe, for example feeding a cable through a conduit. In some example embodiments, the grabber may be configured to tow a payload through the pipe or to a desired position in the pipe. In a biological example, a flexible tube or guide cannula may be towed by the vehicle 200 through a colon. When the vehicle 200 reaches a desired position, the flexible tube may be transitioned to a rigid state, such as by water pressure, or the like. The vehicle may be removed via a tether, such as tether 220, and convention tools may be inserted into the flexible tube to perform a procedure. The positioning of the flexible tube in the colon by the vehicle 200, and then transitioning the flexible tube to the rigid state, may limit or prevent injuries which result from insertion of stiff tubes as guide cannula.

In an example embodiment, the processing circuitry 50 may be in communication with one or more sensors 130. The sensors 130 may include one or more cameras. The cameras may be configured to capture still or moving images of the environment as the vehicle navigates the pipe. In some example embodiments, the sensors 130 may include a distance measurement device configured to determine the distance traveled by the vehicle. In one instance the distance measurement device may determine the distance travels based on the number of times the linear actuator 206 has extended and/or retracted. In some example embodiments, the sensors 130 may include a proximity or range detector. The proximity or range detector may be utilized to determine the distance to an object from a known location or a current position of the vehicle 200, determine wall thickness of the pipe, or the like.

Example Navigation of the Vehicle Through an Enclosed Space

Figure 3:
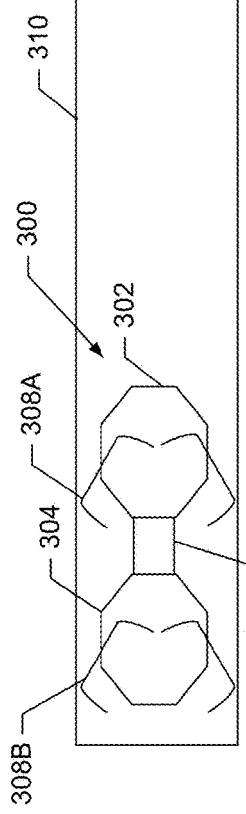
FIGS. 3-6 illustrate an example vehicle navigation of pipe according to an example embodiment.

FIGS. 3-6 illustrate the navigation of a vehicle 300 through an enclosed space, e.g. pipe 310. FIG. 3 illustrates the vehicle 300 in a starting state. In the starting state, a first plurality of claws 308A associated with a head section 302 and a second plurality of claws 308B associated with a tail section 304 are both actuated, e.g. the claws 308A, 308B are engaged with the side wall of the pipe 310. The vehicle also includes a linear actuator 306 which is in a neutral state between full extension and full retraction. It is noted that the starting state depicted in FIG. 3 is merely for illustrative purposes, and one of ordinary skill in the art would immediately appreciate that the vehicle 300 may start navigation of an enclosed space in any state.

Figure 4:
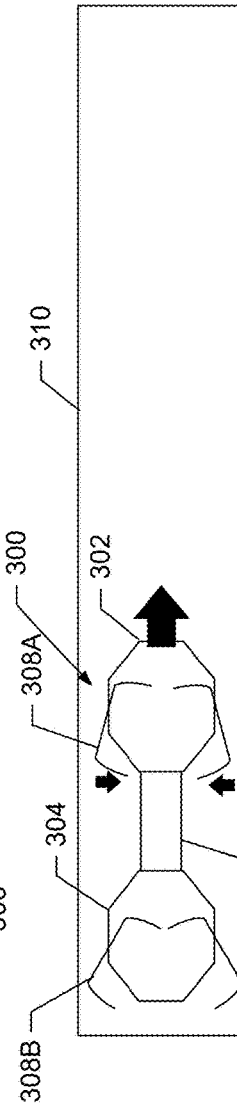

In FIG. 4, the vehicle 300 is depicted in a first navigation state. In the first navigation state, the linear actuator 306 may extend in a first direction, e.g. forward. The second plurality of claws 308B may remain actuated, by pressure of a spring, such as spring 207, and/or claw linear actuators, as discussed above in reference to FIG. 1A. The first plurality of claws 308A may not be actuated, e.g. each of the claws of the first plurality of claws 308A compress the spring 207 to allow travel of the head section 302 and/or the claw linear actuators retract pulling each of the first plurality of claws 308A toward the head section 302. The extension of the linear actuator 306 drives the head section 302 forward in the pipe 310.

Figure 5:
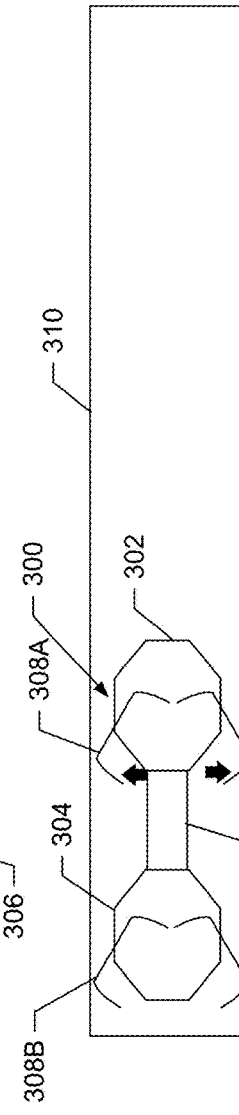

In FIG. 5, the vehicle 300 is depicted in a second navigation state. In the second navigation state, the first plurality of claws 308A may actuate engaging the side wall of the pipe 310. Actuation of the first plurality of claws may 308A include the pressure of the spring 207 pushing each respective claw of the first plurality of claws 308A toward the side wall of the pipe 310 at the cessation of forward motion of the head section 302. Additionally or alternatively, the actuation may include the claw linear actuator associated with each claw of the first plurality of claws 308A to extend pushing each claw toward the side wall of the pipe 310.

Figure 6:
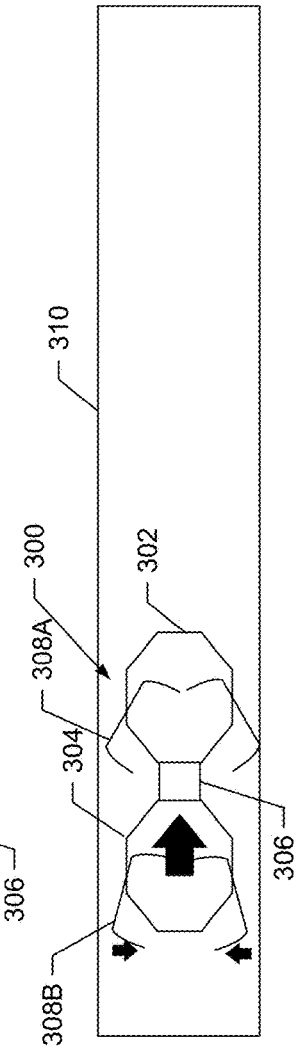

In FIG. 6, the vehicle 300 is depicted in a third navigation state. In the third navigation state, the first plurality of claws 308A may remain actuated, similar to the second plurality of claws 308B in the first navigation state discussed above in reference to FIG. 4. The second plurality of claws 308B associated with the tail section 304 may not be actuated, similar to the first plurality of claws 308A in the first navigation state, as discussed above in reference to FIG. 4. The linear actuator 306 may retract causing the tail section 304 to move forward in the pipe 310. The vehicle may then actuate the second plurality of claws 308B. The vehicle 300 may repeat the navigation process, as necessary, to reach a desire distance or location.

Figure 7:
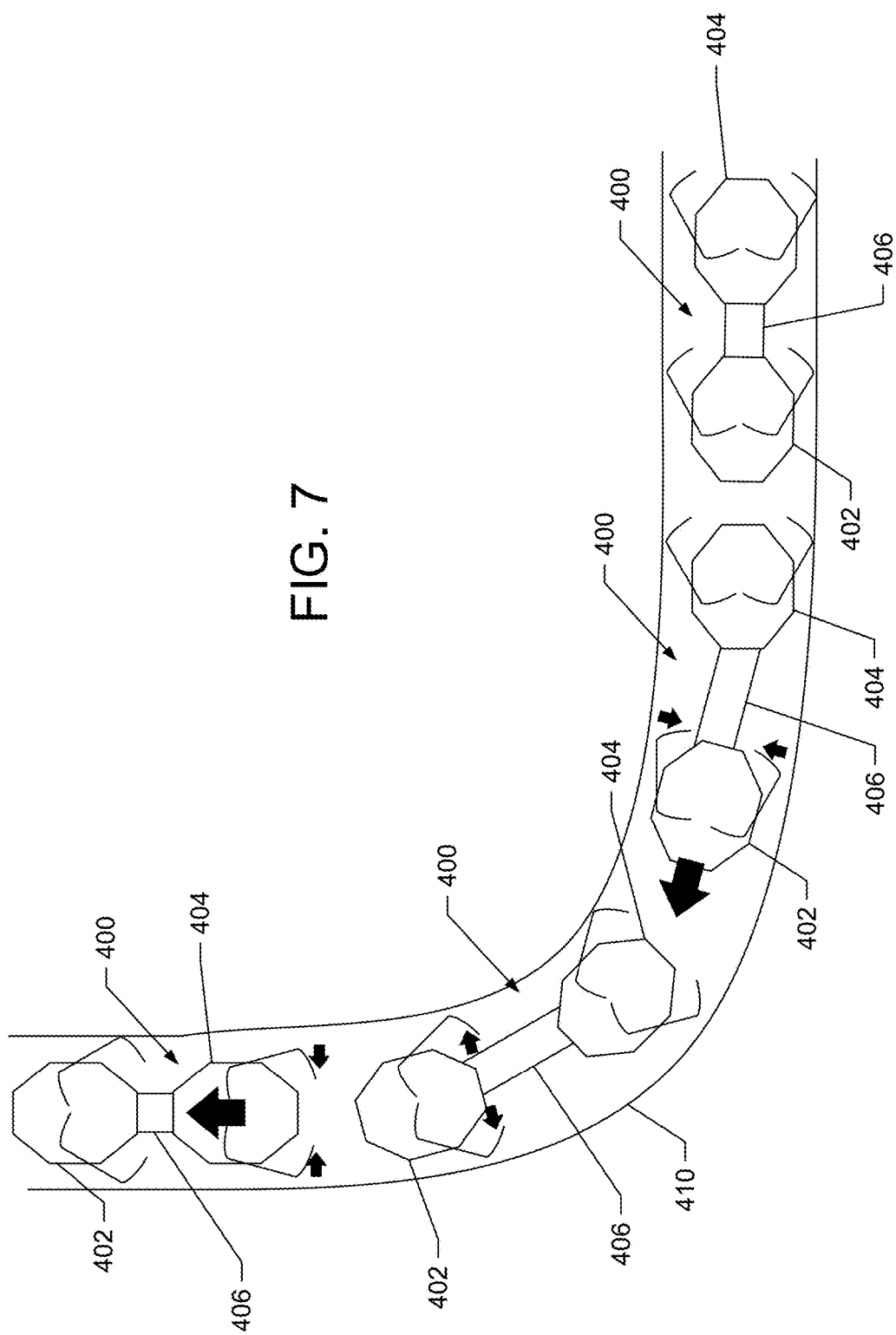
FIG. 7 illustrates a vehicle navigation of a curved pipe according to an example embodiment.

FIG. 7 illustrates a vehicle 400 navigating a bend in an enclosed space, e.g. pipe 410. The vehicle 400 may include a head section 402, a tail section 404, and a linear actuator 406. The head section 402 and tail section 404 may include a first plurality of claws 408A and second plurality of claws 408B, respectively. The linear actuator 406 may be operably coupled to the head section 402 and/or the tail section 404 by an articulated joint or pivot joint, such as a ball joint or rotatable hinge. The articulated joint or ball joint, such as joint 209 discussed above in reference to FIG. 2, may allow for the head section 402 and/or tail section 304 to move or pivot, relative to the linear actuator 406, as the vehicle navigates the turn in the pipe 410. The vehicle 400 may navigate the pipe 410 in substantially the same manner as vehicle 300, as described above in reference to FIGS. 3-6.

Figure 8:
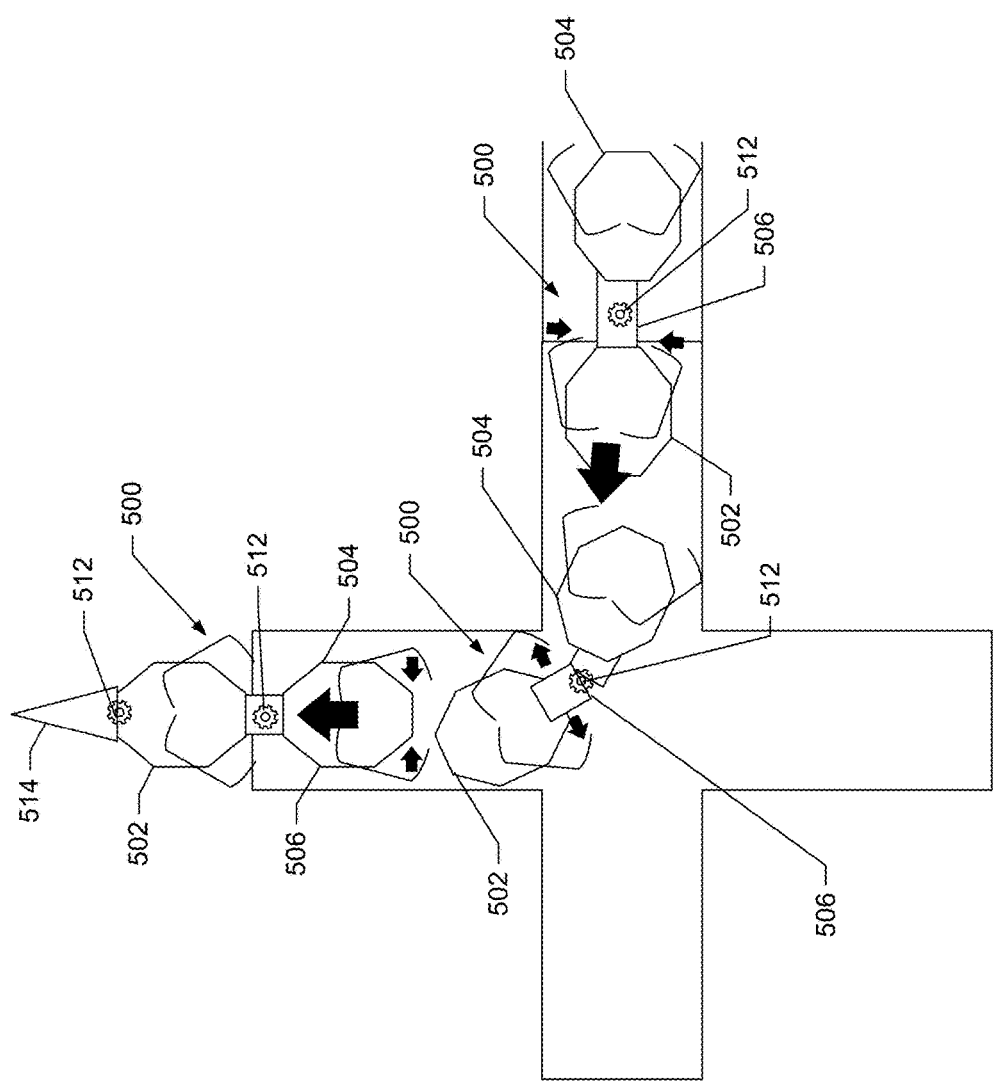
FIG. 8 illustrates a vehicle navigation of a junction of a pipe according to an example embodiment.

FIG. 8 illustrates a vehicle 500 navigating a junction of an enclosed space, e.g. pipe 510. The vehicle 500 may include a head section 502 including a first plurality of claws 508A and a tail section 504 including a second plurality of claws 508B. The head section 502 may be operably coupled to the tail section 504 by a linear actuator 506.

The vehicle 500 may include a servo motor 512 or other steering device configured to steer the head section 502 and/or the tail section 504. Steering of the head section 502 and/or the tail section 504 may enable the vehicle to steer to a desired path at a junction in a pipe 510. Additionally, steering of the head section 502 and/or the tail section may enable macro or micro positioning of a sensor, such as sensor 130, or working element, such as working element 140. Positioning of the sensor 130 and/or working element 140 may enable more precise measurements or work, which may be advantageous in biological environments and/or precision piping systems.

The servo motor 512 may be disposed between the head section 502 and linear actuator 505, between the tail section 504 and linear actuator 506, and/or in a sectioned linear actuator 506. The servo motor 512 may enable steering in the x axis or the x and y axis. The servo motor 512 may enable the vehicle 500 to steer toward a desired portion of pipe 510 at a junction, such as a tee junction of four-way junction. The servo motor 512 may enable the vehicle to navigate tight bends such as 75 degrees, or greater, with relatively short radii and/or sharp turns. The servo motor 512 may enable steering in the x axis or the x and y axis.

Additionally or alternatively, the vehicle 500 may be steered by rotation or movement of an asymmetrical swash plate. The asymmetrical swash plate may be disposed in or at a distal end of the linear actuator 506.

In an example embodiment, the vehicle 500 may, additionally or alternatively, include a forward extension 514. In some example embodiments, the forward extension may be conical, cylindrical, or the like. The forward extension 514 may be fixed or steerable, such as by servo motor 512. The forward extension 514 may be steered toward an opening at a junction to bias the vehicle 500 toward the opening when the forward extension 514 engages the far wall of the opening.

In some embodiments, the vehicle may be further configured for additional operations or optional modifications to. In this regard, in an example embodiment, the vehicle is configured to move backward within the enclosed space by extending the linear actuator, while the second plurality of claws is not actuated and the first plurality of claws is actuated, then retracting the linear actuator, while the second plurality of claws is actuated and the first plurality of claws is not actuated. In some example embodiments, each claw of the first plurality of claws is configured to extend approximately the same distance from the head section when extended and each claw of the second plurality of claws is configured to extend approximately the same distance away from the tail section when extended. In an example embodiment, the extending the first plurality of claws or the second plurality of claws approximately the same distance causes the head section or tail section of the vehicle to be substantially centered in the enclosed space. In some example embodiments, each of the plurality of claws is defined by a complex curve. In an example embodiment, the complex curve enables each of the plurality of claws to have a gripping surface over a full range of extension of each claw from the head section or tail section. In some example embodiments, the first plurality of claws inhibit motion of the head section when actuated and the second plurality of claws inhibit motion of the tail section when actuated. In an example embodiment, the first plurality of claws or second plurality of claws is configured to be extended to a plurality of distances from the head section or tail section, respectively, enabling the vehicle to transition between enclosed spaces of different diameters. In some example embodiments, the operable coupling of the head section or tail section to the linear actuator includes an articulated joint or ball joint. In an example embodiment, the articulated joint enables the vehicle to navigate enclosed spaces that include turns or curves. In some example embodiments, the linear actuator includes a servo configured to steer the head section or tail section. In an example embodiment, the vehicle also includes a working element. In some example embodiments, the working element includes a cutting tool. In an example embodiment, the working element includes a grabber. In some example embodiments the vehicle also includes a sensor. In an example embodiment, the sensor includes a camera. In some example embodiments, the sensor includes a distance measurement device. In an example embodiment, the sensor includes a proximity detector. In some example embodiments, the sensor includes a range detector. In an example embodiment, the enclosed space is a pipe.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring device s are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A vehicle comprising:
   a head section comprising a selectively actuated first plurality of claws;
   a tail section comprising a selectively actuated second plurality of claws;
   a linear actuator operably coupling the head section to the tail section;
   a claw actuator operably coupling at least one of the head section and the tail section to claws of at least one of the first and second plurality of claws; and
   a switchable lock operably coupled to the claws,
   wherein the linear actuator is configured to be selectively extended and retracted,
   wherein the vehicle is configured to move forward within an enclosed space by extending the linear actuator, while the first plurality of claws is not actuated and the second plurality of claws is actuated, then retracting the linear actuator, while the first plurality of claws is actuated and the second plurality of claws is not actuated, and wherein the claws are defined by a complex curve, are constructed entirely of a semi rigid material, and are configured to deform against a wall of the enclosed space such that a contact surface area of the claws increases.

2. The vehicle of claim 1, wherein the vehicle is configured to move backward within the enclosed space by extending the linear actuator, while the second plurality of claws is not actuated and the first plurality of claws is actuated, then retracting the linear actuator, while the second plurality of claws is actuated and the first plurality of claws is not actuated.

3. The vehicle of claim 1, wherein each claw of the first plurality of claws is configured to extend approximately the same distance from the head section when extended and each claw of the second plurality of claws is configured to extend approximately the same distance away from the tail section when extended.

4. The vehicle of claim 3, wherein the extending the first plurality of claws or the second plurality of claws approximately the same distance causes the head section or tail section of the vehicle to be substantially centered in the enclosed space.

5. The vehicle of claim 1, wherein the complex curve enables each of the plurality of claws to have a gripping surface over a full range of extension of each claw from the head section or tail section.

6. The vehicle of claim 1, wherein the first plurality of claws inhibit motion of the head section when actuated and the second plurality of claws inhibit motion of the tail section when actuated.

7. The vehicle of claim 1, wherein the first plurality of claws or second plurality of claws is configured to be extended to a plurality of distances from the head section or tail section, respectively, enabling the vehicle to transition between enclosed spaces of different diameters.

8. The vehicle of claim 1, wherein the operable coupling of the head section or tail section to the linear actuator comprises an articulated joint or ball joint.

9. The vehicle of claim 8, wherein the articulated joint enables the vehicle to navigate enclosed spaces that include turns or bends.

10. The vehicle of claim 1, wherein the linear actuator comprises a servo configured to steer the head section or tail section.

11. The vehicle of claim 1 further comprising a working element.

12. The vehicle of claim 11, wherein the working element comprises a cutting tool.

13. The vehicle of claim 11, wherein the working element comprises a grabber.

14. The vehicle of claim 1 further comprising a sensor.

15. The vehicle of claim 14, wherein the sensor comprises a camera.

16. The vehicle of claim 14, wherein the sensor comprises a distance measurement device.

17. The vehicle of claim 14, wherein the sensor comprises a proximity detector.

18. The vehicle of claim 14, wherein the sensor comprises a range detector.

19. The vehicle of claim 1, wherein the enclosed space is a pipe or tubular biological cavity.

* * * * *